Oct. 5, 1971 W. C. HILL Plant Pat. 3,067
APRICOT TREE
Filed Sept. 18, 1969
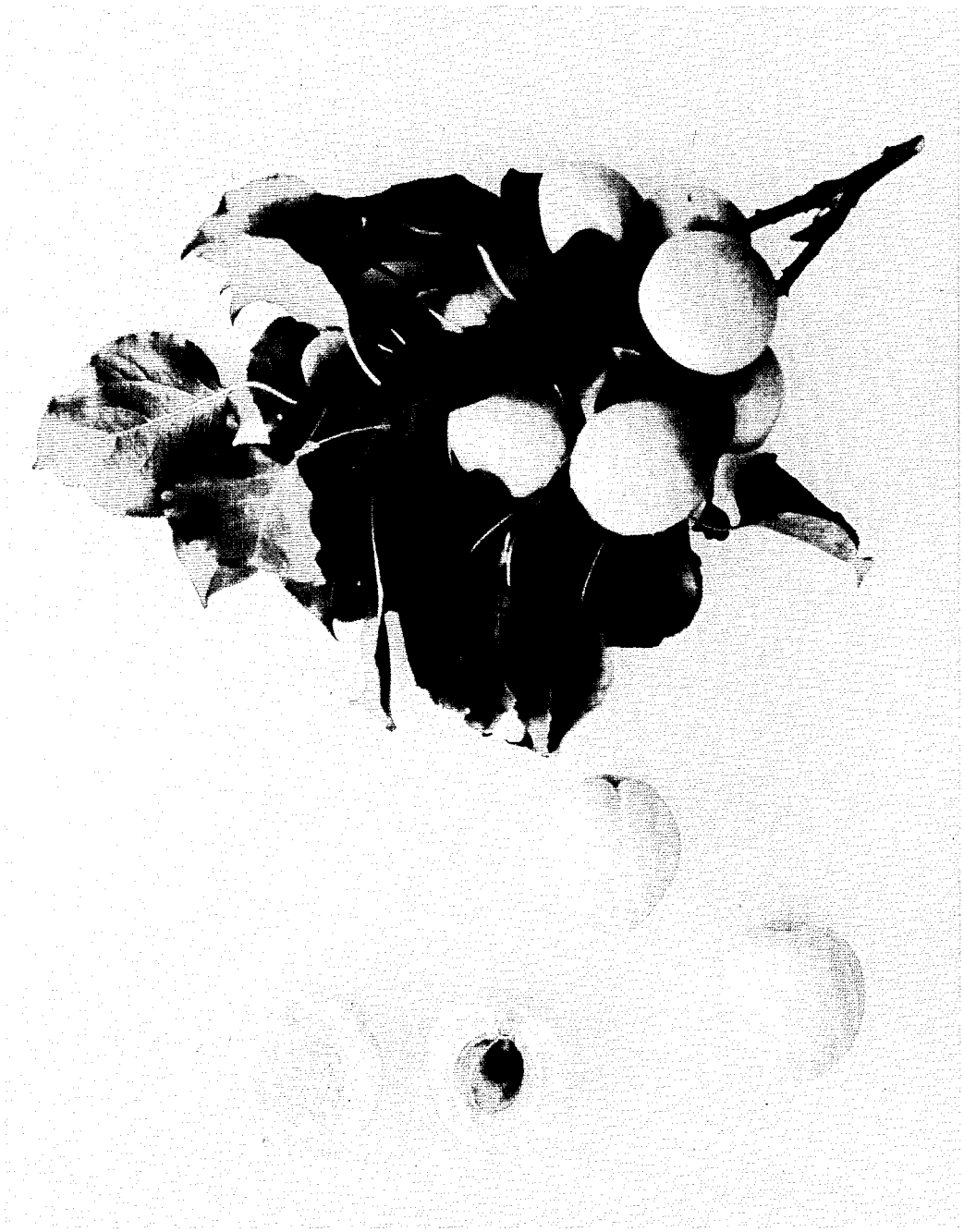
INVENTOR
Willard Clayton Hill
BY
Webster & Webster
ATTORNEYS United States Patent Office Plant Pat. 3,067
Patented Oct. 5, 1971

3,067

APRICOT TREE

Willard Clayton Hill, Visalia, Calif., assignor to
L. E. Cooke Co., Visalia, Calif.

Filed Sept. 18, 1969, Ser. No. 859,216
Int. Cl. A01h 5/03
U.S. Cl. Plt.—39 1 Claim

ABSTRACT OF THE DISCLOSURE

A large, vigorous, upright, dense, vase-formed apricot tree which is self-fertile and a regular and very productive bearer of large, freestone fruit; the tree having unusually long and progressive blooming and ripening periods, and the fruit being substantially resistant to pit burn.

ORIGIN OF THE VARIETY

The herein claimed new and distinct variety of apricot tree was originated by me on my ranch located near Visalia, Tulare County, Calif., in the following manner:

Seeds from two adjoining apricot trees, one a Tilton and one a Blenheim (both unpatented), were planted and the resultant seedlings grown under careful and continuing observation; one such seedling—which is the present variety—having evidenced certain distinctive characteristics, and, therefore, such one seedling was selected by me for asexual reproduction.

As the seeds were intermingled before planting, it is not known which of the above varieties was the seed parent.

ASEXUAL REPRODUCTION OF THE VARIETY

Subsequent to origination of the present variety, it was asexually reproduced by budding; i.e. buds from the original tree were placed on rootstock seedlings; such budding having been undertaken on my behalf by a commercial nursery. The rootstock seedlings thus budded were planted on my ranch located as aforesaid, and—when they came into bearing—such asexual reproductions ran true to the original tree in all respects.

SUMMARY OF THE VARIETY

The herein claimed new and distinct variety of apricot tree is large, vigorous, upright, dense, vase-formed, self-fertile, and a regular and very productive bearer of large, freestone fruit; the variety being importantly characterized by unusually long and progressive blooming and ripening periods, each of at least three weeks duration. While the fruit individually ripens evenly, the over-all crop on the tree ripens progressively during the harvest period of the unusually long duration mentioned above; i.e. only a portion of the crop being ripe and ready for picking at any given point of time in such harvest period. The advantage of such progressive ripening of the fruit resides in the fact that such characteristic makes the tree extremely desirable for home gardens in that fresh fruit is provided over a span of time much longer than normal to other varieties.

The herein claimed new and distinct variety of apricot tree is further importantly characterized by an apparent substantial resistance to pit burn. Neither the original tree of the variety nor any of the asexual reproductions thereof have experienced any pit burn, while known varieties—such as the Tilton, Blenheim, and others—growing in the same agricultural area and under identical weather conditions have evidenced occurrences of such defect.

BRIEF DESCRIPTION OF THE DRAWING

The drawing is an illustration, by photographic reproduction in color, of a twig with fruit and leaves, and detached fruit; one detached fruit being cut into halves to expose the flesh, and with the stone remaining in one such half.

DESCRIPTION OF THE VARIETY

The botanical details of this new and distinct variety of apricot tree—with color definitions referenced to Maerz and Paul Dictionary of Color—are as follows:

Tree:
- *Size.*—Large.
- *Vigor.*—Vigorous.
- *Growth.*—Upright.
- *Density.*—Dense.
- *Shape.*—Vase-formed.
- *Production.*—Very productive.
- *Bearing.*—Regular bearer.

Trunk:
- *Size.*—Medium.
- *Texture.*—Medium.

Branches:
- *Size.*—Medium.
- *Texture.*—Medium.

Lenticels:
- *Number.*—Medium.

Leaves:
- *Size.*—Medium; average length—3½"; average width—2⅝".
- *Form.*—Cordate; acutely pointed.
- *Thickness.*—Medium.
- *Texture.*—Smooth.
- *Color.*—Top side—medium green (22–L–9); under side—lighter green (22–K–8).
- *Margin.*—Crenate.
- *Petiole.*—Medium length; medium thickness.
- *Glands.*—Number—1 to 4; alternate; medium size; usually positioned 2 on blade and 1 to 3 on petiole.
- *Stipules.*—None.

Flower buds:
- *Size.*—Medium.
- *Length.*—Medium.
- *Form.*—Conic.

Flowers:
- *Blooming period.*—Unusually long and progressive, extending over a period of at least 3 weeks.
- *Date of first bloom.*—Feb. 15, 1969.
- *Date of last bloom.*—Mar. 10, 1969.

Fruit:
- *Maturity when described.*—Eating ripe—July 10, 1969.
- *Harvesting period.*—Unusually long and progressive, extending over a period of at least 3 weeks.
- *Date of first picking.*—July 1, 1969.
- *Date of last picking.*—July 25, 1969.
- *Size.*—Uniform; large; average diameter axially —2"; average transversely in suture plane—2¼".
- *Form.*—Uniform; symmetrical; oblong—broadly conical.
- *Suture.*—Distinct; extends from base to apex.
- *Ventral surface.*—Rounded slightly.
- *Lips.*—Equal.
- *Cavity.*—Elongated in suture plane, with suture showing on one side; average depth—¼"; average breadth—⅝".
- *Base.*—Rounded.
- *Apex.*—Short.

Skin:

*Thickness.*—Medium.

*Texture.*—Medium.

*Tenacity.*—Tenacious to flesh.

*Tendency to crack.*—None.

*Color.*—Apricot yellow (11–K–8).

Flesh:

*Color.*—Apricot yellow (11–L–9); surface of pit cavity—Apricot yellow (11–L–9).

*Texture.*—Firm; fine; meaty; melting.

*Fibers.*—Few.

*Ripens.*—Fruit individually ripens evenly. Crop ripens progressively as described.

*Flavor.*—Subacid; delicate; vinous.

*Eating quality.*—Good to best.

Stone:

*Type.*—Free.

*Size.* — Large; average length—1⅛″; Average breadth—⅞″; average thickness—7/16″.

*Form.*—Oblong.

*Base.*—Oblique.

*Hilum.*—Broad.

*Apex.*—Rounded.

*Sides.*—Equal.

*Ventral edge.*—Thick.

*Dorsal edge.*—Full.

*Tendency to split.*—None.

*Color.*—Light brown (7–A–11).

Use: Market—local; dessert; culinary; canning.

Keeping quality:—Good.

Resistance to insects and diseases: No unusual susceptibilities noted.

Shipping quality: Good.

The apricot tree and its fruit herein described may vary in slight detail due to climatic and soil conditions under which the variety may be grown; the present description being of the variety as grown in the general vicinity of Visalia, Tulare County, Calif.

I claim:

1. A new and distinct variety of apricot tree, substantially as illustrated and described, which is large, vigorous, upright, dense, vase-formed, self-fertile, and a regular and very productive bearer of large, freestone fruit; the variety being particularly characterized by unusually long and progressive blooming and ripening periods, each of at least three weeks duration, and further characterized by a substantial resistance to pit burn.

No references cited.

ROBERT E. BAGWILL, Primary Examiner